US009855417B2

(12) United States Patent
Barker et al.

(10) Patent No.: US 9,855,417 B2
(45) Date of Patent: Jan. 2, 2018

(54) METHOD OF MAKING AN ELECTRODE ARRAY HAVING EMBEDDED ELECTRODES

(71) Applicant: BOSTON SCIENTIFIC NEUROMODULATION CORPORATION, Valencia, CA (US)

(72) Inventors: John Michael Barker, Ventura, CA (US); Aditya Vasudeo Pandit, Costa Mesa, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 692 days.

(21) Appl. No.: 14/486,842

(22) Filed: Sep. 15, 2014

(65) Prior Publication Data

US 2015/0000124 A1  Jan. 1, 2015

Related U.S. Application Data

(62) Division of application No. 13/159,040, filed on Jun. 13, 2011, now Pat. No. 8,868,206.

(Continued)

(51) Int. Cl.
*H01R 43/00* (2006.01)
*A61N 1/05* (2006.01)

(52) U.S. Cl.
CPC ....... *A61N 1/0534* (2013.01); *Y10T 29/49117* (2015.01)

(58) Field of Classification Search
CPC ............... A61N 1/0534; A61N 1/0551; Y10T 29/49117; Y10T 29/49174; Y10T 29/49176; Y10T 29/49204

(Continued)

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/286,940, filed May 23, 2014.

(Continued)

*Primary Examiner* — Donghai D Nguyen
(74) *Attorney, Agent, or Firm* — Lowe Graham Jones PLLC; Bruce E. Black

(57) ABSTRACT

A method of manufacturing a device for brain stimulation includes forming a lead body having a distal end section and coupling at least one pre-electrode to the distal end section of the lead body. The pre-electrode defines a divider with a plurality of partitioning arms, and has a plurality of fixing lumens. A portion of the pre-electrode aligned with the portioning arms is removed to divide the pre-electrode into a plurality of segmented electrodes. Each of the plurality of segmented electrodes defines at least one of the plurality of fixing lumens at least partially disposed through the segmented electrode. A material is introduced through the at least one fixing lumen to couple the plurality of segmented electrodes to the lead body.

13 Claims, 13 Drawing Sheets

Related U.S. Application Data

(60) Provisional application No. 61/356,529, filed on Jun. 18, 2010.

(58) Field of Classification Search
USPC .......... 29/825, 857, 858, 874; 607/115, 116
See application file for complete search history.

(56) References Cited

U.S. PATENT DOCUMENTS

| | | | |
|---|---|---|---|
| 4,744,370 | A | 5/1988 | Harris |
| 5,000,194 | A | 3/1991 | van den Honert et al. |
| 5,135,001 | A | 8/1992 | Sinofsky et al. |
| 5,374,285 | A | 12/1994 | Vaiani et al. |
| 5,458,629 | A | 10/1995 | Baudino et al. |
| 5,522,874 | A | 6/1996 | Gates |
| 5,711,316 | A | 1/1998 | Elsberry et al. |
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,134,478 | A | 10/2000 | Spehr |
| 6,161,047 | A | 12/2000 | King et al. |
| 6,167,311 | A | 12/2000 | Rezai |
| 6,322,559 | B1 | 11/2001 | Daulton et al. |
| 6,343,226 | B1 | 1/2002 | Sunde et al. |
| 6,510,347 | B2 | 1/2003 | Borkan |
| 6,556,873 | B1 | 4/2003 | Smits |
| 6,560,472 | B2 | 5/2003 | Hill et al. |
| 6,564,078 | B1 | 5/2003 | Marino et al. |
| 6,678,564 | B2 | 1/2004 | Ketterl et al. |
| 6,757,970 | B1 | 7/2004 | Kuzma et al. |
| 7,006,859 | B1 | 2/2006 | Osorio et al. |
| 7,027,852 | B2 | 4/2006 | Helland |
| 7,047,084 | B2 | 5/2006 | Erickson et al. |
| 7,190,989 | B1 | 3/2007 | Swanson et al. |
| 7,203,548 | B2 | 4/2007 | Whitehurst et al. |
| 7,285,118 | B1 | 10/2007 | Lozano |
| 7,292,890 | B2 | 11/2007 | Whitehurst et al. |
| 7,489,971 | B1 | 2/2009 | Franz |
| 7,668,601 | B2 | 2/2010 | Hegland et al. |
| 7,761,985 | B2 | 7/2010 | Hegland et al. |
| 7,809,446 | B2 | 10/2010 | Meadows |
| 7,822,482 | B2 | 10/2010 | Gerber |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,974,705 | B2 | 7/2011 | Zdeblick et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,099,177 | B2 | 1/2012 | Dahlberg |
| 8,225,504 | B2 | 7/2012 | Dye et al. |
| 8,295,944 | B2 | 10/2012 | Howard et al. |
| 8,321,025 | B2 | 11/2012 | Bedenbaugh |
| 8,359,107 | B2 | 1/2013 | Pianca et al. |
| 8,391,985 | B2 | 3/2013 | McDonald |
| 8,583,237 | B2 | 11/2013 | Bedenbaugh |
| 8,649,873 | B2 | 2/2014 | Moffitt et al. |
| 9,381,348 | B2 * | 7/2016 | Romero ............... A61N 1/0551 |
| 2001/0023368 | A1 | 9/2001 | Black et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0168805 | A1 | 8/2006 | Hegland et al. |
| 2006/0247697 | A1 | 11/2006 | Sharma et al. |
| 2007/0038279 | A1 | 2/2007 | Fifer et al. |
| 2007/0168007 | A1 | 7/2007 | Kuzma et al. |
| 2007/0203546 | A1 | 8/2007 | Stone et al. |
| 2007/0219551 | A1 | 9/2007 | Honour et al. |
| 2008/0077186 | A1 | 3/2008 | Thompson et al. |
| 2008/0103580 | A1 | 5/2008 | Gerber |
| 2008/0114230 | A1 | 5/2008 | Addis |
| 2008/0139913 | A1 | 6/2008 | Schulman |
| 2008/0215125 | A1 | 9/2008 | Farah et al. |
| 2008/0255647 | A1 | 10/2008 | Jensen et al. |
| 2009/0054941 | A1 | 2/2009 | Eggen et al. |
| 2009/0204192 | A1 | 8/2009 | Carlton et al. |
| 2010/0030298 | A1 | 2/2010 | Martens et al. |
| 2010/0036468 | A1 | 2/2010 | Decre et al. |
| 2010/0076535 | A1 | 3/2010 | Pianca et al. |
| 2010/0077606 | A1 | 4/2010 | Black et al. |
| 2010/0082076 | A1 | 4/2010 | Lee et al. |
| 2010/0094387 | A1 | 4/2010 | Pianca et al. |
| 2010/0100152 | A1 | 4/2010 | Martens et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1 | 10/2011 | Schulte et al. |
| 2011/0301665 | A1 | 12/2011 | Mercanzini et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2013/0109254 | A1 | 5/2013 | Klardie et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0317587 | A1 | 11/2013 | Barker |
| 2013/0325091 | A1 | 12/2013 | Pianca et al. |
| 2014/0039587 | A1 | 2/2014 | Romero |
| 2014/0039590 | A1 | 2/2014 | Moffitt et al. |
| 2014/0088666 | A1 | 3/2014 | Goetz et al. |
| 2014/0123484 | A1 | 5/2014 | DiGiore et al. |
| 2014/0142671 | A1 | 5/2014 | Moffitt et al. |
| 2014/0155971 | A1 | 6/2014 | Pianca et al. |
| 2014/0180375 | A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009/001327 A2 | 12/2008 |
| WO | 2009025816 A1 | 2/2009 |
| WO | 2009102536 A1 | 8/2009 |
| WO | 2010/055421 A1 | 5/2010 |
| WO | 2010/060011 A2 | 5/2010 |

(56) References Cited

FOREIGN PATENT DOCUMENTS

| | | |
|---|---|---|
| WO | 2013162775 A2 | 10/2013 |
| WO | 2014018092 A1 | 1/2014 |

OTHER PUBLICATIONS

U.S. Appl. No. 14/286,889, filed May 23, 2014.
U.S. Appl. No. 14/286,829, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/286,934, filed May 23, 2014.
International Search Report and Written Opinion for International Patent Application No. PCT/US2011/040229, dated Dec. 19, 2011.
Official Communication for U.S. Appl. No. 13/159,040, dated May 14, 2014.
Official Communication for U.S. Appl. No. 13/159,040, dated Jun. 4, 2013.
Official Communication for U.S. Appl. No. 13/159,040, dated Feb. 8, 2013.
U.S. Appl. No. 14/469,214, filed Aug. 26, 2014.
U.S. Appl. No. 14/557,211, filed Dec. 1, 2014.
International Search Report and Written Opinion for International Patent Application No. PCT/US2011/040229 dated Dec. 19, 2011.

\* cited by examiner

US 9,855,417 B2

METHOD OF MAKING AN ELECTRODE ARRAY HAVING EMBEDDED ELECTRODES

CROSS-REFERENCE TO RELATED APPLICATIONS

This application is a divisional of U.S. patent application Ser. No. 13/159,040 filed Jun. 13, 2011 which claims the benefit under 35 U.S.C. §119(e) of U.S. Provisional Patent Application Ser. No. 61/356,529 filed on Jun. 18, 2010, both of which are incorporated herein by reference.

FIELD

The invention is directed to devices and methods for brain stimulation including deep brain stimulation. In addition, the invention is directed to devices and method for brain stimulation using a lead having embedded segmented electrodes

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

BRIEF SUMMARY

One embodiment is a method of manufacturing a device for brain stimulation. The method includes forming a lead body having a distal end section and coupling at least one pre-electrode to the distal end section of the lead body. The pre-electrode defines a divider with a plurality of partitioning arms, and has a plurality of fixing lumens. A portion of the pre-electrode aligned with the portioning arms is removed to divide the pre-electrode into a plurality of segmented electrodes. Each of the plurality of segmented electrodes defines at least one of the plurality of fixing lumens at least partially disposed through the segmented electrode. A material is introduced through the at least one fixing lumen to couple the plurality of segmented electrodes to the lead body.

Another embodiment is a device for brain stimulation that includes an insulative tubing having a distal end section and at least one electrode frame disposed on the distal end section of the insulative tubing. The at least one electrode frame is formed of an insulative material. Each of the at least one electrode frame defines at least one electrode cavity. The device also includes a plurality of segmented electrodes with at least one of the plurality of segmented electrodes disposed within each of the at least one electrode cavity.

Yet another embodiment is a method of manufacturing a device for brain stimulation. The method includes forming an insulative carrier having a plurality of apertures for receiving a plurality of segmented electrodes and coupling a plurality of segmented electrodes to the insulative carrier. One of the plurality of segmented electrodes is disposed within each of the plurality of apertures and each of the plurality of segmented electrodes has at least one flange for securing the segmented electrode within the insulative carrier. The method also includes wrapping the insulative carrier around a mandrel to form a cylindrical lead body.

A further embodiment is a method of manufacturing a device for brain stimulation. The method includes forming an insulative tubing having a distal end section and forming at least one conductor lumen through the insulative tubing. The at least one conductor lumen extends longitudinally through the insulative tubing. The method further includes introducing a plurality of electrode tubes through the at least one conductor lumen of the insulative tubing, and removing a portion of the outer surface of the insulative tubing to expose a portion of a one of the at least one electrode tube

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of concentric windowed cylinders.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No. 12/237,888 ("Leads With Non-Circular-Shaped Distal Ends For Brain Stimulation Systems and Methods of Making and Using"). Each of these references is incorporated herein by reference in its respective entirety.

Figure 13:
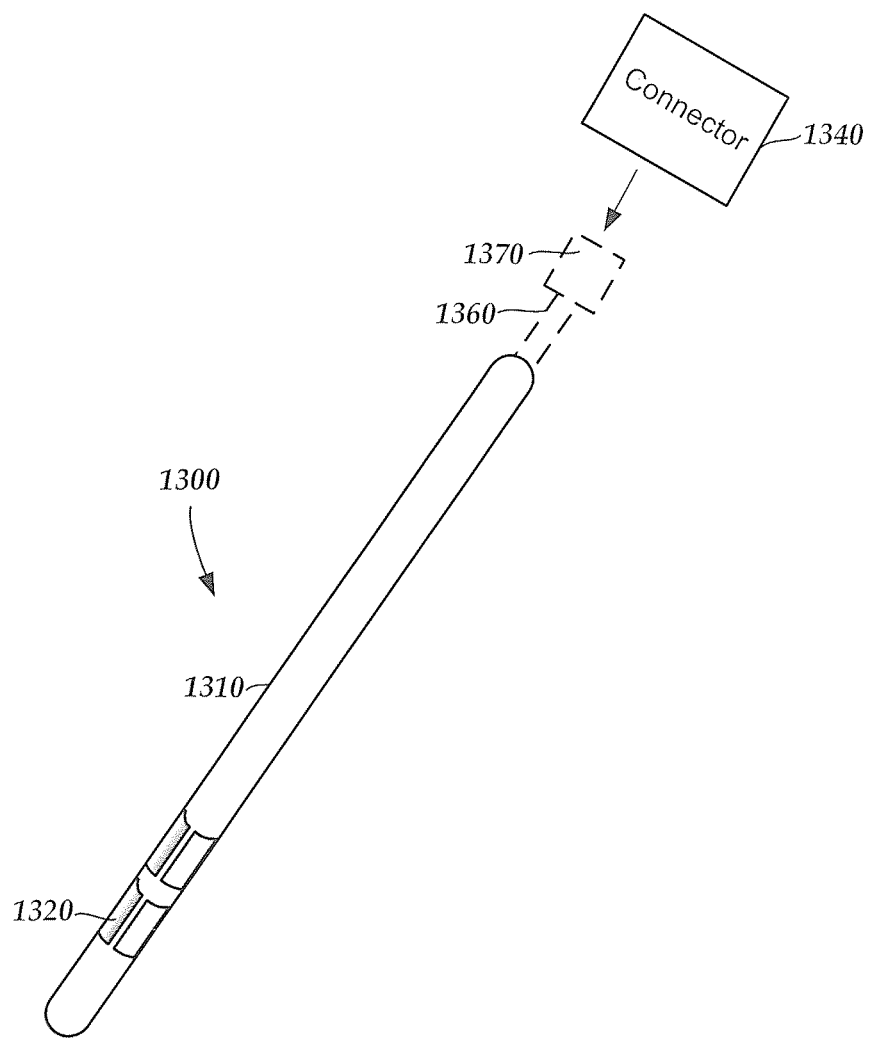
FIG. 13 is a schematic side view of one embodiment of a device for brain stimulation, according to the invention.

FIG. 13 illustrates one embodiment of a device 1300 for brain stimulation. The device includes a lead 1310, segmented electrodes 1320, a connector 1340 for connection of the electrodes to a control unit, and a stylet 1360 for assisting in insertion and positioning of the lead in the patient's brain. The stylet 1360 can be made of a rigid material. Examples of suitable materials include tungsten, stainless steel, or plastic. The stylet 1360 may have a handle 1370 to assist insertion into the lead, as well as rotation of the stylet and lead. The connector 1340 fits over the proximal end of the lead 1310, preferably after removal of the stylet 1360.

In one example of operation, access to the desired position in the brain can be accomplished by drilling a hole in the patient's skull or cranium with a cranial drill (commonly referred to as a burr), and coagulating and incising the dura mater, or brain covering. The lead 1310 can be inserted into the cranium and brain tissue with the assistance of the stylet 1360. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead, retract the lead, or rotate the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

It will be understood that the lead 1310 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, radially segmented electrode arrays may be useful for selectively simulating tissue.

Figure 1A:
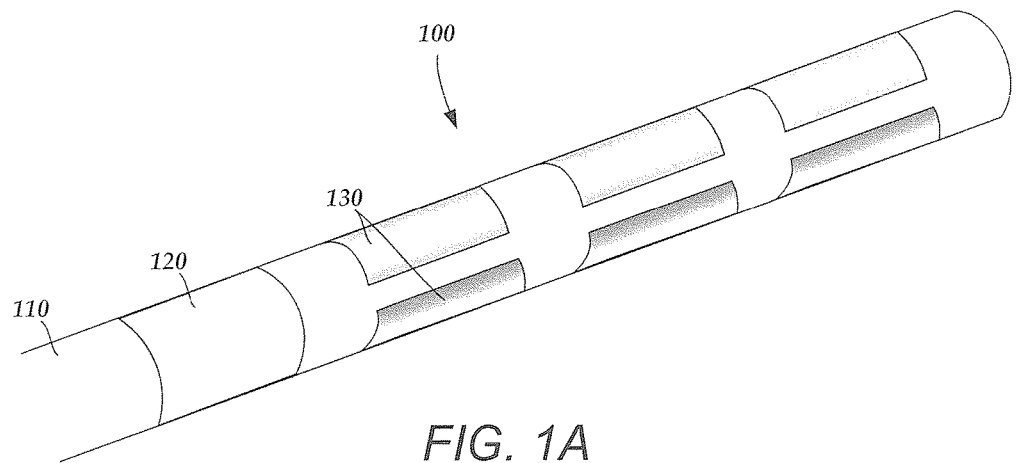
FIG. 1A is a schematic perspective view of one embodiment of a portion of a lead having a plurality of segmented electrodes and a ring electrode, according to the invention.

FIG. 1A illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyurethanes, polyether polyurethane, polycarbonate polyurethane, or silicone-polyurethane copolymer. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. For example, in FIG. 1B, the segmented electrodes 130 are shown as portions of a ring or curved rectangular portions. In some other embodiments, the segmented electrodes 130 are curved square portions. The shape of the segmented electrodes 130 may also be substantially triangular, diamond-shaped, oval, circular or spherical. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Stimulation electrodes in the form of ring electrodes 120 may be disposed on any part of the lead body 110, usually near a distal end of the lead. FIG. 1A illustrates a portion of a lead having one ring electrode. Any number of ring electrodes may be disposed along the length of the lead body 110. For example, the lead body may have one ring electrode, two ring electrodes, three ring electrodes or four ring electrodes. In some embodiments, the lead will have five, six, seven or eight ring electrodes. Other embodiments do not include ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 1B:
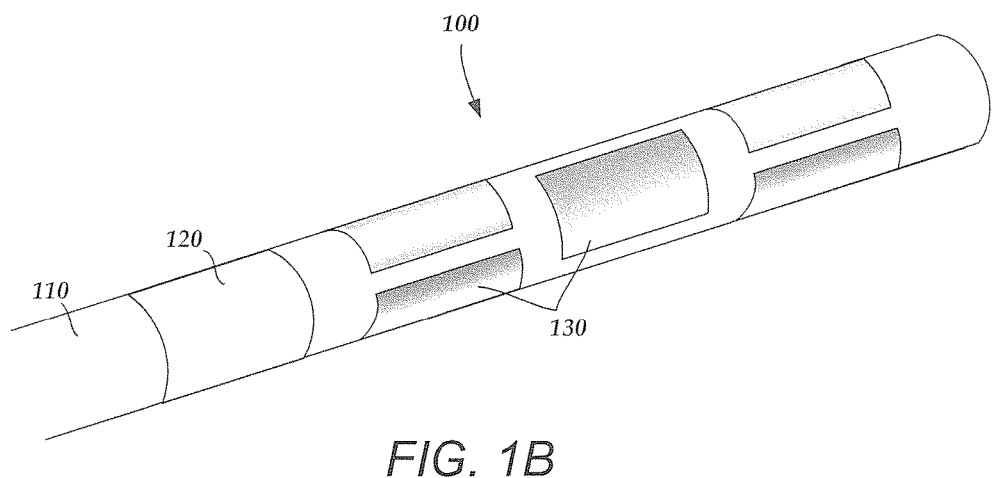
FIG. 1B is a schematic perspective view of another embodiment of a lead having a plurality of segmented electrodes arranged in staggered orientation and a ring electrode, according to the invention.

FIG. 1B is a schematic perspective view of another embodiment of a lead having a plurality of segmented electrodes. As seen in FIG. 1B, the plurality of segmented electrodes 130 may be arranged in different orientations relative to each other. In contrast to FIG. 1A, where the three sets of segmented electrodes are aligned along the length of the lead body 110, FIG. 1B displays another embodiment in which the three sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including three sets of segmented electrodes. These three sets of segmented electrodes 130 may be disposed in different configurations. For example, three sets of segmented electrodes 130 may be disposed on the distal end of the lead body 110, distal to a ring electrode 120. Alternatively, three sets of segmented electrodes 130 may be disposed proximal to a ring electrode 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
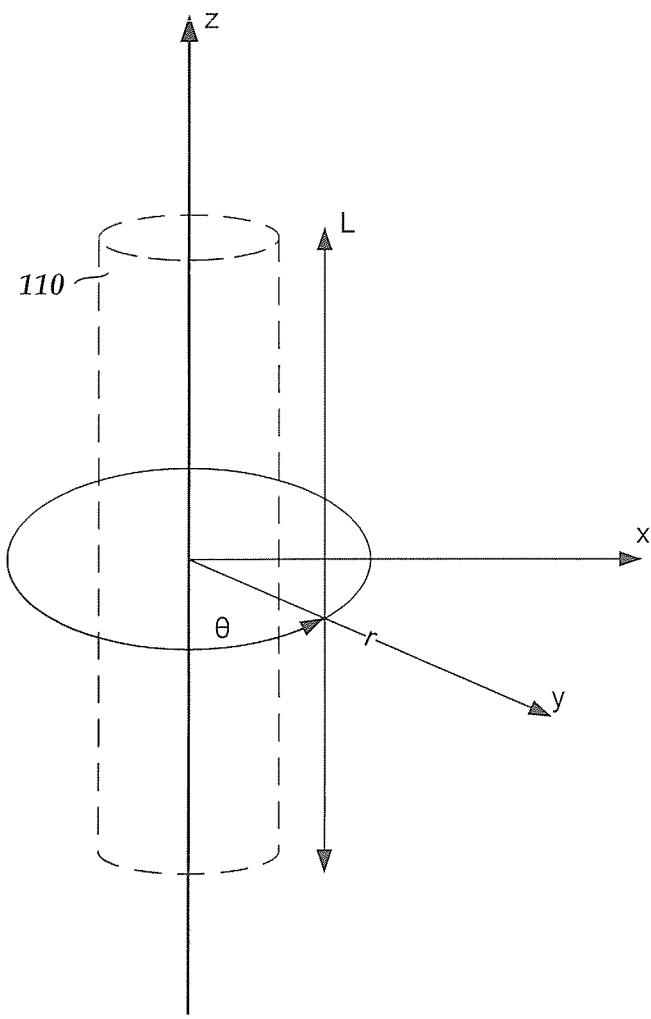
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

In addition to 360° selectivity, a lead having segmented electrodes may provide several advantages. First, the lead may provide for more directed stimulation, as well as less "wasted" stimulation (i.e. stimulation of regions other than the target region). By directing stimulation toward the target tissue, side effects may be reduced. Furthermore, because stimulation is directed toward the target site, the battery in an implantable pulse generator may last for a longer period of time between recharging.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Radially segmented electrode arrays may be manufactured in a variety of ways, for example, by embedding or coupling conductive portions in a lead body. In at least some embodiments, a disk having an inner cavity may be used to form a radially segmented electrode array. The disk may define various lumens for housing conductors and for facilitating attachment to the lead body. Radially segmented electrode arrays may also be formed by disposing electrodes in an electrode frame or in a lumen defined by the lead body.

Figure 3A:
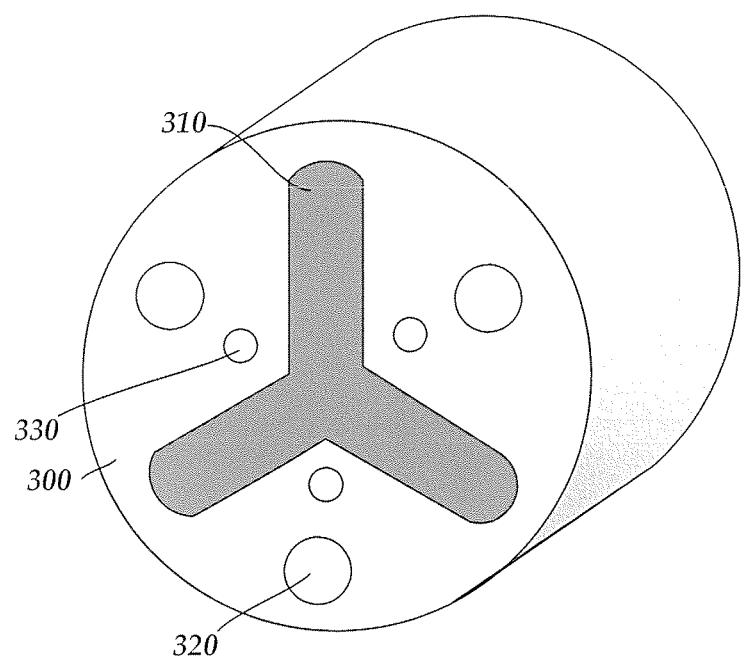
FIG. 3A is a schematic perspective view of one embodiment of a pre-electrode, according to the invention.

In some embodiments a pre-electrode is used to form a radially segmented electrode array. FIG. 3A is a schematic perspective view of one embodiment of a pre-electrode disk 300. The pre-electrode may be formed of a conductor such as a metal, alloy, conductive oxide, or any other suitable conductive material. In some embodiments, the pre-electrode 300 is formed of platinum, platinum-iridium, iridium, 316L stainless steel, tantalum, nitinol or a conductive polymer. The shape and size of the pre-electrode 300 may be modified. As seen in FIG. 3A, the pre-electrode 300 may be formed in the shape of a disk. In some embodiments, the pre-electrode 300 is formed of a substantially cylindrical member having a diameter larger than the desired final diameter of the lead. It will be understood that the pre-electrode 300 need not be substantially cylindrical, but may also be formed in the shape of a cube (see e.g., FIG. 3B), or any other polyhedron. In such embodiments, a cylindrical lead may be obtained by grinding (e centerless grinding), machining, or ablating the outer diameter of the pre-electrode 300.

The pre-electrode 300 defines a divider 310. The divider 310 may be formed of any shaped passage that extends through the longitudinal axis of the pre-electrode 300. As seen in FIG. 3A, in some embodiments, the divider 310 is formed of a central passage having three partitioning arms. The three partitioning arms will divide the pre-electrode 300 into three segmented electrodes as will be described with reference to FIGS. 4, 5A and 5B. It will be understood that the size and shape of the divider 310 may be varied and that the divider 310 may be formed in any pattern suitable for dividing the pre-electrode 300 into a desired number of partitions. In some embodiments, the divider also includes a central lumen for passage of a stylet.

The pre-electrode 300 may include one or more conductor lumens 320. The conductor lumen 320 may be any lumen, hole, or passage that extends through the longitudinal axis of the pre-electrode 300. In some embodiments, the pre-electrode 300 includes one, two, three, four, five, six, eight, ten, or twelve conductor lumens 320. In some embodiments, the pre-electrode 300 includes one conductor lumen 320 for each segmented electrode that will be formed from the pre-electrode 300. For example, if a divider 310 is configured such that three segmented electrodes will be formed from the pre-electrode 300, then three conductor lumens 320 may be formed, one for each segmented electrode. The size of the conductor lumens 320 may be varied as needed. In some embodiments, the conductor lumens 320 are defined to have a circular cross-section corresponding to the cross-section of conductors that will be coupled to the electrodes. In some embodiments, the cross-section of the conductor lumens 320 are the same size and shape. Alternatively, the conductor lumens 320 may be formed in different shapes or sizes. For example, the conductor lumen 320 may have a cross-section that is in the shape of a square, a rectangle, an oval, or a triangle.

In some embodiments, the pre-electrode 300 includes one or more fixing lumens 330. The fixing lumen 330 may be any lumen, hole, or passage that extends through the longitudinal axis of the pre-electrode 300. In some embodiments, the fixing lumen 330 only partially extends through the longitudinal axis of the electrode 300. In at least some other embodiments, the fixing lumen 330 is defined as a through hole, a passage that extends through the full length of the pre-electrode 300. The fixing lumen 330 may be similar to the conductor lumen 320 in shape and size. The fixing lumen 330 may also be of different shape or size than the conductor lumen 320. In some embodiments, the fixing lumen 330 has a circular cross-section. As seen in FIG. 3A, the fixing lumen 330 may have a smaller cross-section than the conductor lumen 320.

Figure 3B:
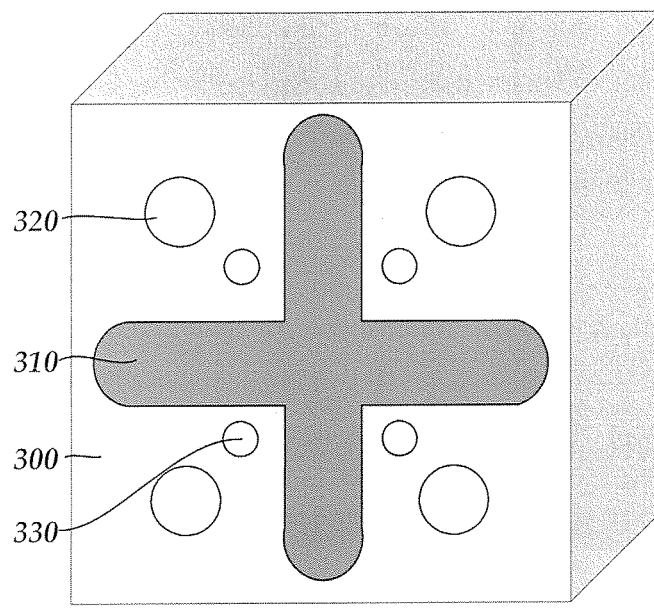
FIG. 3B is a schematic perspective view of a second embodiment of a pre-electrode, according to the invention.

FIG. 3B is a schematic perspective view of a second embodiment of a pre-electrode 300. The pre-electrode 300 of FIG. 3B includes fixing lumens 330 and conductor lumens 320. The pre-electrode 300 also includes a divider 310 with four partitioning arms. As previously noted, a divider 310 may include any number of partitioning arms such as three, four, five, six, eight, ten, or twelve portioning arms. Thus, a single pre-electrode 300 may be used to form four segmented electrodes. As can be seen in FIG. 3B, the pre-electrode 300 is formed in the shape of a cube. The cube-shaped pre-electrode 300 may be further processed to form segmented electrodes having the desired shape and size.

Figure 4:
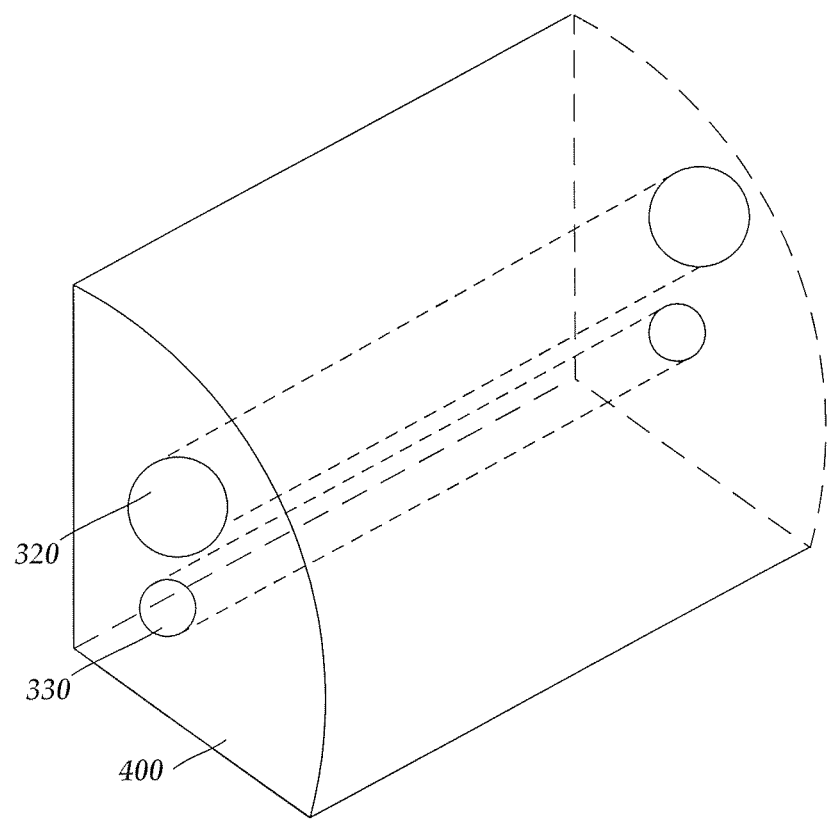
FIG. 4 is a schematic perspective view of one embodiment of a segmented electrode, according to the invention.

FIG. 4 is a schematic perspective view of one embodiment of a segmented electrode 400. The segmented electrode 400 may be the result of partitioning the pre-electrode 300 of FIG. 3A along divider 310. In some embodiments, after partitioning the pre-electrode 300, each segmented electrode 400 includes a single fixing lumen 330 and a single conductor lumen 320. It will be understood that the pre-electrodes 300 and segmented electrodes 400 may be configured such that each segmented electrode 400 includes any number of fixing lumens 330 or conductor lumens 320.

Figure 5A:
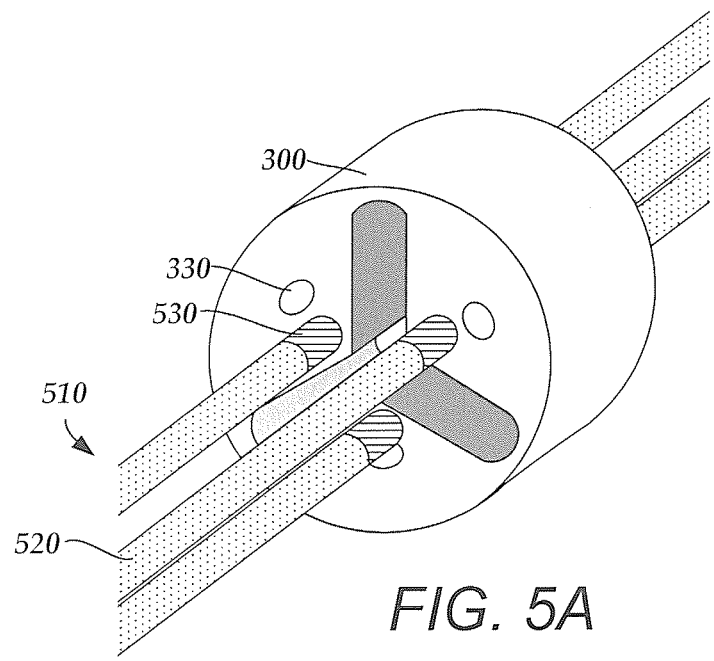
FIG. 5A is a schematic perspective view of one embodiment of a pre-electrode disk coupled to conductors, according to the invention.

FIG. 5A is a schematic perspective view of one embodiment of a pre-electrode 300 before grinding. Although the pre-electrode 300 of FIG. 5A is disk-shaped, the pre-electrode 300 may be formed of any suitable shape. The pre-electrode 300 includes a plurality of fixing lumens 330. The fixing lumens 330 allow for coupling or locking portions of the pre-electrode 300 to the lead body 110 (not shown) by reflowing a portion of the lead body 110 to allow it to pass through the fixing lumens 330. In some embodiments, additional fixing material similar to the lead body 110 is disposed within the fixing lumen 330. The fixing material may be composed of the same material or any other material capable of reflowing with the lead body 110. In some embodiments, portions of the pre-electrode 300 are further bonded to the lead body 110 with a potting agent or adhesive such as epoxy.

FIG. 5A further illustrates conductors 510 being disposed through the conductor lumens 320. In some embodiments, the conductors 510 have a diameter corresponding to the diameter of the conductor lumens 320. As seen in FIG. 5A, a conductor 510 may be coated or wrapped with an insulator 520. The conductors 510 may also include ablated portions 530. The ablated portions 530 allow for electrical coupling between the conductor 510 and the segmented electrode. In some embodiments, the portions of the conductors 510 are disposed within the conductor lumens 320 of the pre-electrode 300 then welded to a portion of the pre-electrode 300. It will be understood than any other method suitable for electrically coupling a pre-electrode 300 to a conductor 510 may be used.

The pre-electrodes 300 may be formed larger in diameter than the lead body 110. Furthermore, the pre-electrodes 300 is yet undivided. In some embodiments, it may be useful or desirable to grind down the pre-electrode 300 to an appropriate diameter. After the pre-electrodes 300 have been ground down to the same level as the lead body 110, the lead 100 is isodiametric, having substantially the same diameter in all directions. The result is a substantially cylindrical lead 100 that is suitable for deep brain stimulation. Grinding down the pre-electrodes 300 is also capable of forming segmented electrodes 400 from the pre-electrodes 300. Preferably, the pre-electrodes are ground after the pre-electrodes are fixed within the lead and coupled to the conductors.

Figure 5B:
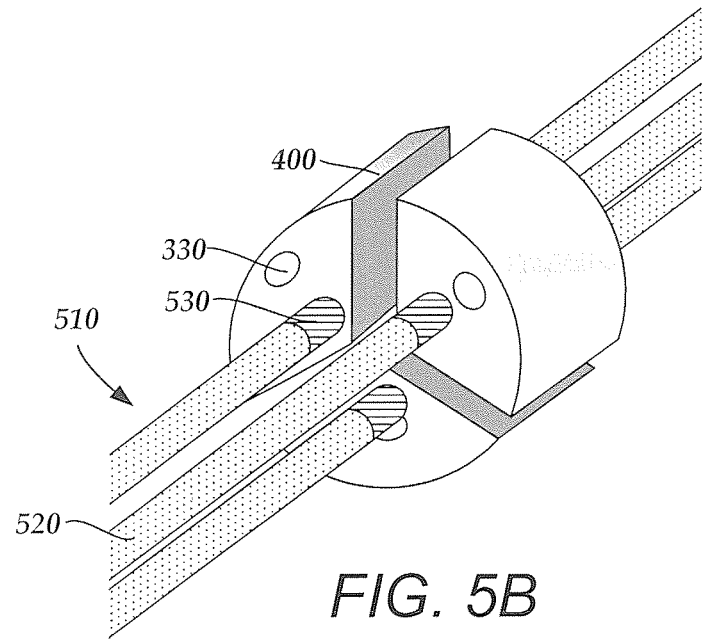
FIG. 5B is a schematic perspective view of the pre-electrode disk of FIG. 5A after centerless grinding, according to the invention.

FIG. 5B is a schematic perspective view of the pre-electrode 300 of FIG. 5A after grinding. In some embodiments, grinding the pre-electrode 300 results in grinding portions of the pre-electrode down to the divider 310, thus forming separate segmented electrodes 400. As can be appreciated from FIG. 5B, three segmented electrodes 400 are formed at one level of the lead body 110. A plurality of pre-electrodes 300 may be disposed at predetermined longitudinal levels of the lead body 100 to create leads having variable stimulation profiles. In some embodiments, the segmented electrodes 400 are electrically insulated from one another so that the stimulation directed to each segmented electrode 400 is independently-controlled.

Figure 6A:
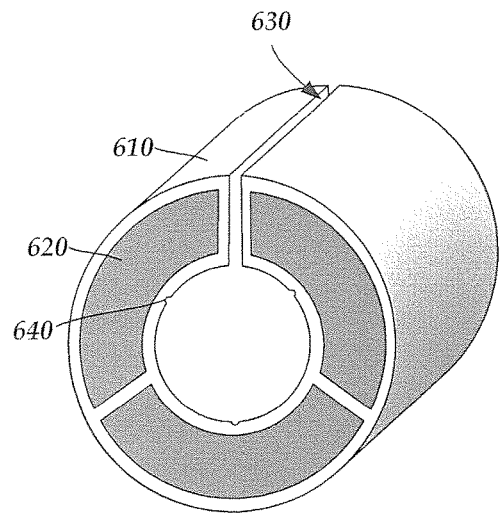
FIG. 6A is a schematic perspective view of one embodiment of an electrode frame, according to the invention.

In some other embodiments a pre-formed electrode frame may be used to form a lead having a plurality of segmented electrodes. FIG. 6A illustrates an electrode frame 610 capable of housing a plurality of segmented electrodes. The electrode frame 610 may be formed of a biocompatible, non-conducting material such as, for example, a polymeric material. Suitable polymeric materials include, but are not limited to, polyetheretherketone (PEEK), polytetrafluoroethylene (e.g., Teflon™), polyimide, silicone, polyurethanes, polyether polyurethane, polycarbonate polyurethane, and silicone-polyurethane copolymer.

The electrode frame 610 defines a plurality of electrode chambers 620 for accepting a plurality of segmented electrodes. The embodiment of FIG. 6A illustrates an electrode frame 610 having three electrode chambers 620. It will be understood that the electrode frame 610 may include any number of electrode chambers 620. In some embodiments, the electrode frame 610 includes one, two, three, four, five, six, seven, eight, nine, ten, twelve, fourteen or sixteen electrode chambers 620. The electrode chambers 620 may also be defined to house segmented electrodes of the same or different shape or size. In at least some embodiments, the electrode chambers 620 are of the same shape and size. In some embodiments, the electrode chambers 620 fully enclose the segmented electrodes. The electrode chambers 620 may be equally spaced about the electrode frame 610. As illustrated, in some embodiments, the electrode frame 610 is C-shaped with an opening 630 configured for coupling the electrode frame 610 to a tubing as will be described in greater detail with reference to FIG. 10A. The electrode frame 610 may also include longitudinally extending grooves 640 on the interior of the electrode frame 610. The grooves 640 may be configured to house conductors (not shown).

Figure 6B:
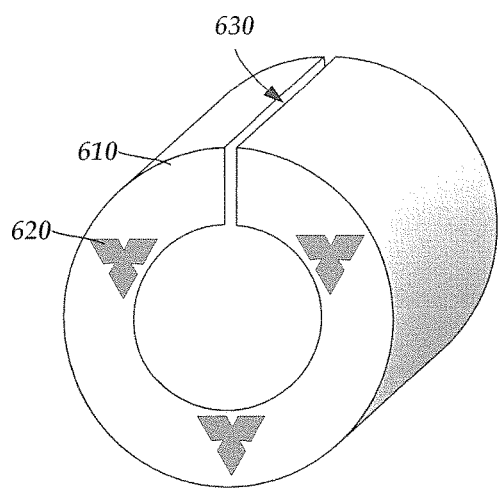
FIG. 6B is a schematic perspective view of a second embodiment of an electrode frame, according to the invention.
Figure 6C:
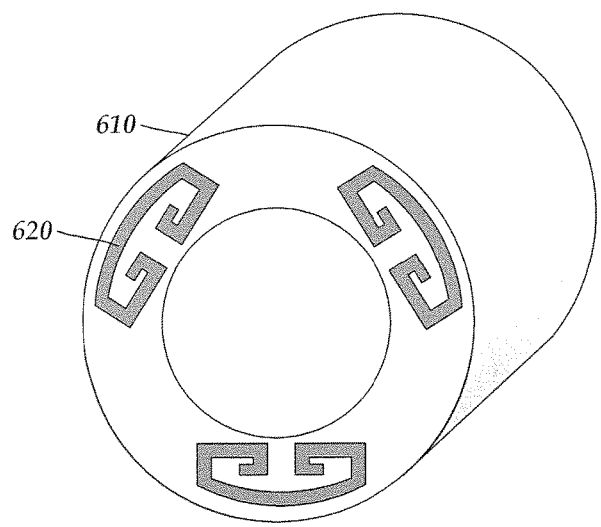
FIG. 6C is a schematic perspective view of a third embodiment of an electrode frame, according to the invention.

FIGS. 6B and 6C are schematic perspective views of a second and third embodiment of an electrode frame 610. As seen in FIGS. 6B and 6C, the electrode frames 610 may include various electrode chambers 620 with a variety of different shapes. For example, the electrode frames 610 may be formed to house different-shaped segmented electrodes. As seen in FIG. 6C, in some embodiments, the electrode frame 610 lacks an opening 636, but is formed slightly larger in diameter so as to be press fit over the lead body.

Figure 7A:
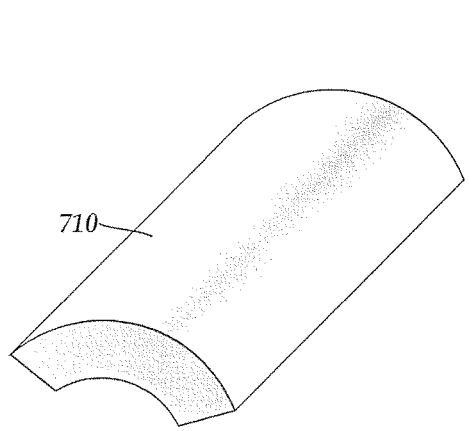
FIG. 7A is a schematic perspective view of one embodiment of a segmented electrode corresponding to the electrode frame of FIG. 6A, according to the invention.
Figure 7B:
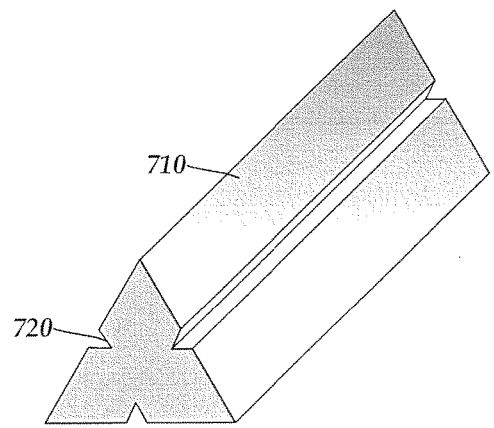
FIG. 7B is a schematic perspective view of a second embodiment of a segmented electrode corresponding to the electrode frame of FIG. 6B, according to the invention.
Figure 7C:
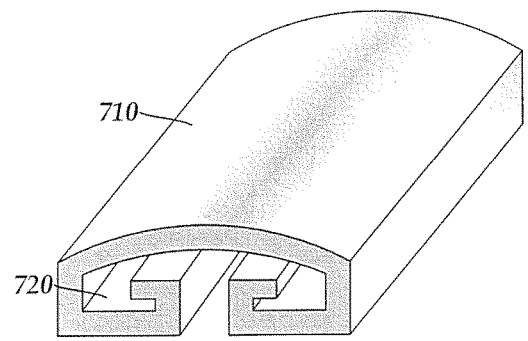
FIG. 7C is a schematic perspective view of a third embodiment of a segmented electrode corresponding to the electrode frame of FIG. 6C, according to the invention.

The segmented electrodes 710 may be formed of platinum, platinum-iridium, iridium, 316L stainless steel, tantalum, nitinol, a conductive polymer, or any other suitable conductive material. FIG. 7A is a schematic perspective view of one embodiment of a segmented electrode 710 corresponding to the electrode frame 610 of FIG. 6A, formed of an elongate member with an arched cross-section. FIG. 7B is a schematic perspective view of a second embodiment of a segmented electrode 710 corresponding to the electrode frame 610 of FIG. 6B. The segmented electrode 710 of FIG. 7B has a triangular cross-section. FIG. 7C is a schematic perspective view of a third embodiment of a segmented electrode 710 corresponding to the electrode frame 610 of FIG. 6C. A seen in FIGS. 7A-C, the segmented electrodes 710 may be formed in a variety of shapes and sizes. In some embodiments, the segmented electrodes 710 are formed of elongate members having a circular, ovoid, rectangular, square, hexagonal, star-shaped, cruciform, trapezoidal, or a patterned cross-section (e.g. the cross-section shown in FIG. 7C). As seen in FIGS. 7B and 7C, in some embodiments, the segmented electrodes 710 include fastening features 720 to aid in fastening them to the electrode frame 610. For example, the fastening feature 720 may be any of a hole, key, seam, neck, shoulder, or rib.

Figure 8:
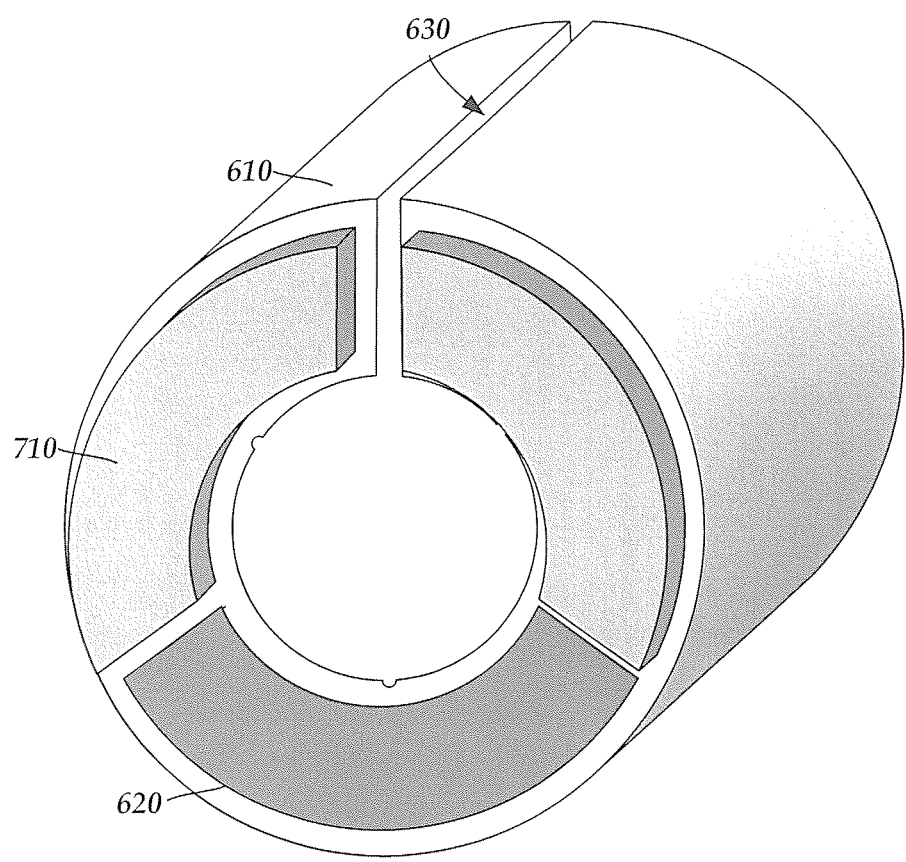
FIG. 8 is a schematic perspective view of the segmented electrodes of FIG. 7A being press fit into the electrode frame of FIG. 6A, according to the invention.

FIG. 8 is a schematic perspective view of the segmented electrodes 710 of FIG. 7A being inserted into the electrode chambers 620 of the electrode frame 610 of FIG. 6A. As seen in FIG. 8, the segmented electrode 710 may be press fit into the electrode frame 610. Other methods may be used to further affix or couple the segmented electrode 710 to the electrode frame 610. For example, a potting agent or adhesive may be used to affix the segmented electrode 710 to the electrode frame 610. In at least some embodiments, fastening features 720, which correspond to the shape of the electrode chambers 620 are useful for maintaining a proper fit between an electrode frame 610 and a segmented electrode 710.

Figure 9A:
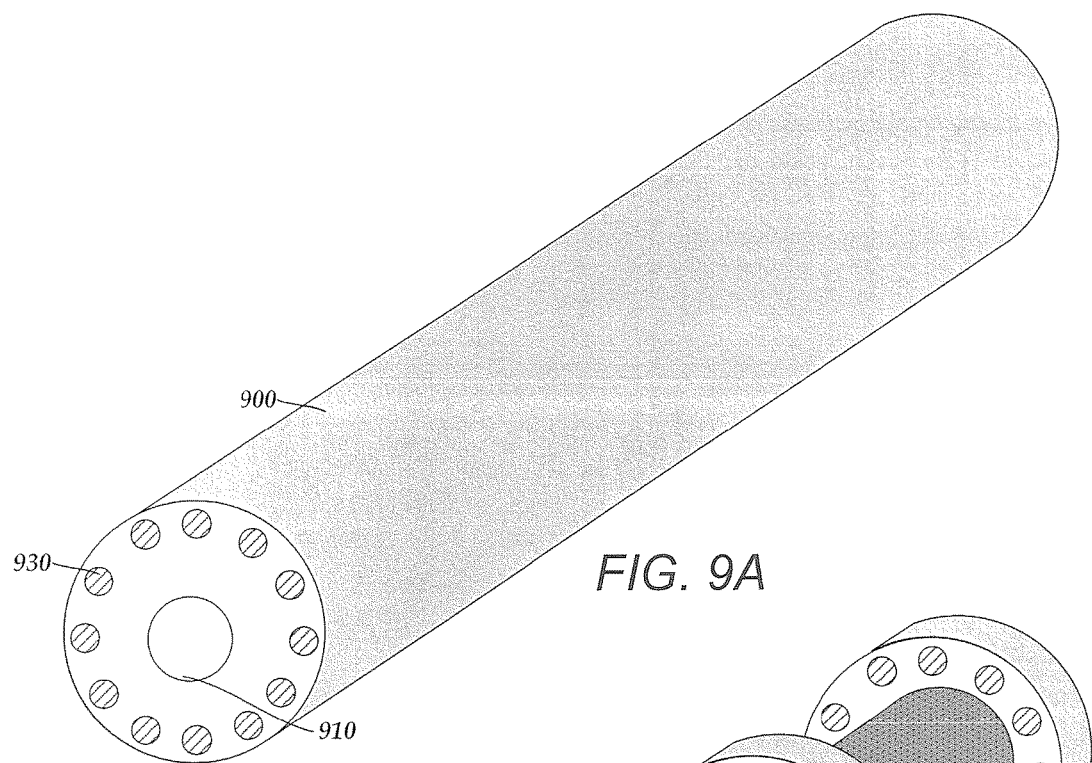
FIG. 9A is a schematic perspective view of one embodiment of a multi-lumen tubing, according to the invention.

FIG. 9A is a schematic perspective view of one embodiment of a multi-lumen tubing 900. The multi-lumen tubing 900 may be formed of any material or combination of materials used in forming a lead body. The multi-lumen tubing 900 may define a central passage 910 configured to receive a stylet or other insertion instrument. Though the central passage 910 is illustrated as a passage having a circular cross-section, any shaped central passage 910 may be formed. In some embodiments, the central passage 910 has a cross-section corresponding to the cross-section of a stylet. The multi-lumen tubing 900 may define a plurality of longitudinally disposed conductor lumens 930. Any number of conductor lumens 930 may be defined within the multi-lumen tubing 900. In some embodiments, one, two, three, four, five, six, seven, eight, nine, ten, twelve or more conductor lumens 930 may be defined by the multi-lumen tubing 900. In some embodiments, the number of conductor lumens 930 corresponds to the number of electrodes that will be disposed on the tubing 900.

Figure 9B:
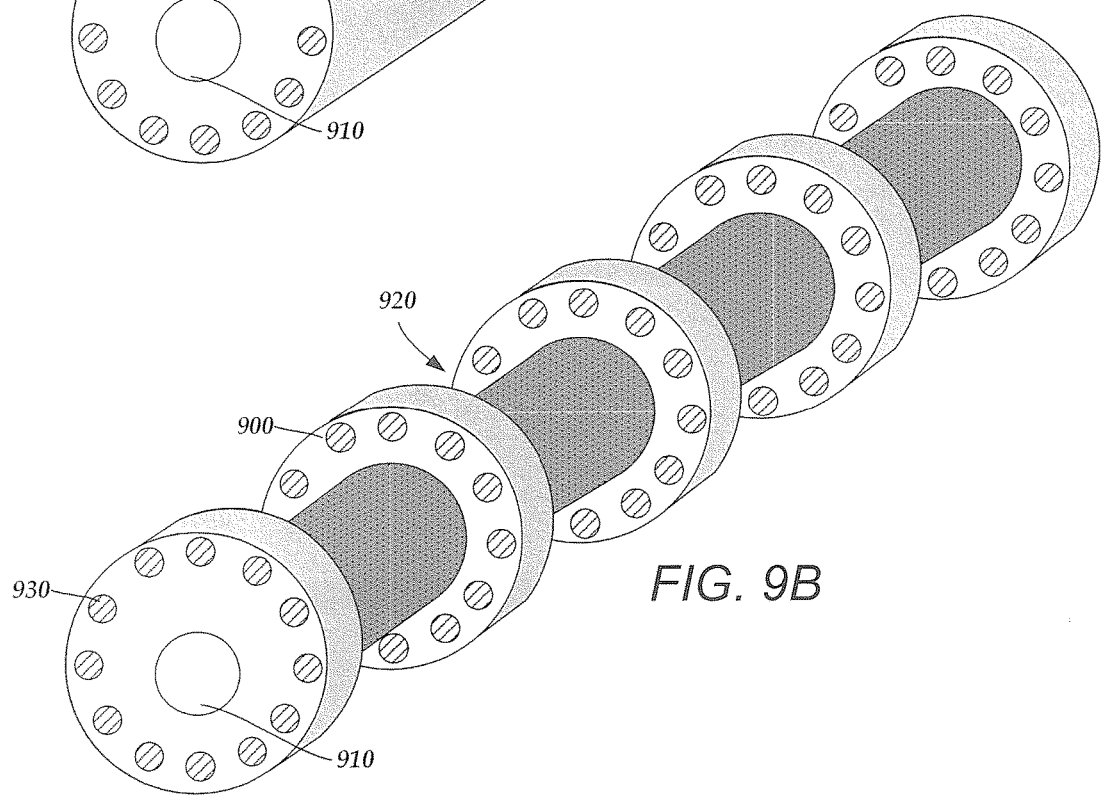
FIG. 9B is a schematic perspective view of the multi-lumen tubing of FIG. 9A after ablating portions of the tubing, according to the invention.

Portions of the multi-lumen tubing 900 may be removed to allow the coupling of the electrode frame 610. FIG. 9B is a schematic perspective view of the multi-lumen tubing 900 of FIG. 9A after ablating portions of the tubing 900. It will be understood that any method may be used for removing sections of multi-lumen tubing 900. For example, portions of the multi-lumen tubing 900 may be ground down to form slots 920. Alternatively, slots 920 may also be formed by ablating the outer layer of the multi-lumen tubing 900 using, for example, laser ablation. The resulting slots 920 may have dimensions corresponding to the dimensions of the electrode frame 610, so that the electrode frame 610 is coupleable to the multi-lumen tubing 900.

Figure 10A:
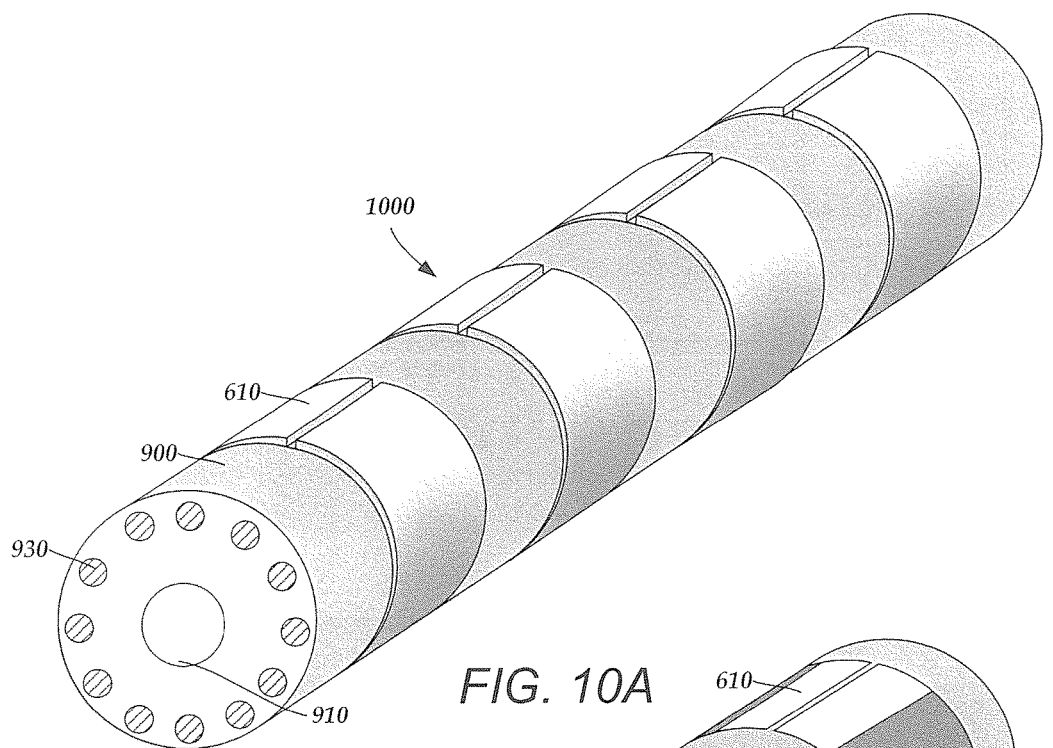
FIG. 10A is a schematic perspective view of one embodiment of a lead consisting of a multi-lumen tubing and electrode frames having a plurality of segmented electrodes, according to the invention.

The electrode frames 610 may be coupled to the multi-lumen tubing 900. FIG. 10A is a schematic perspective view of one embodiment of a lead consisting of a multi-lumen tubing 900 and electrodes frames 610 disposed on the tubing 900. In some embodiments, the electrode frame 610 is flexible and configured so that the opening 630 of the electrode frame 610 allows coupling to the multi-lumen tubing 900. In at least some other embodiments, the electrode frames 610 are configured to slide over the tubing 900. After coupling the electrode frames 610 and the multi-lumen tubing 900, the tubing 900 and the electrode frame 610 may be reflowed to form a lead 1000. In some embodiments, the tubing 900 and electrode frames 610 are configured so that during the reflow process, material is reflowed through fixing lumens. By reflowing material through the fixing lumen, a more reliable lead 1000 may be formed that is less prone to breakage and failure. Individual conductors may be disposed through conductor lumens 930 and the grooves 640 and welded to the individual segmented electrodes 710.

Figure 10B:
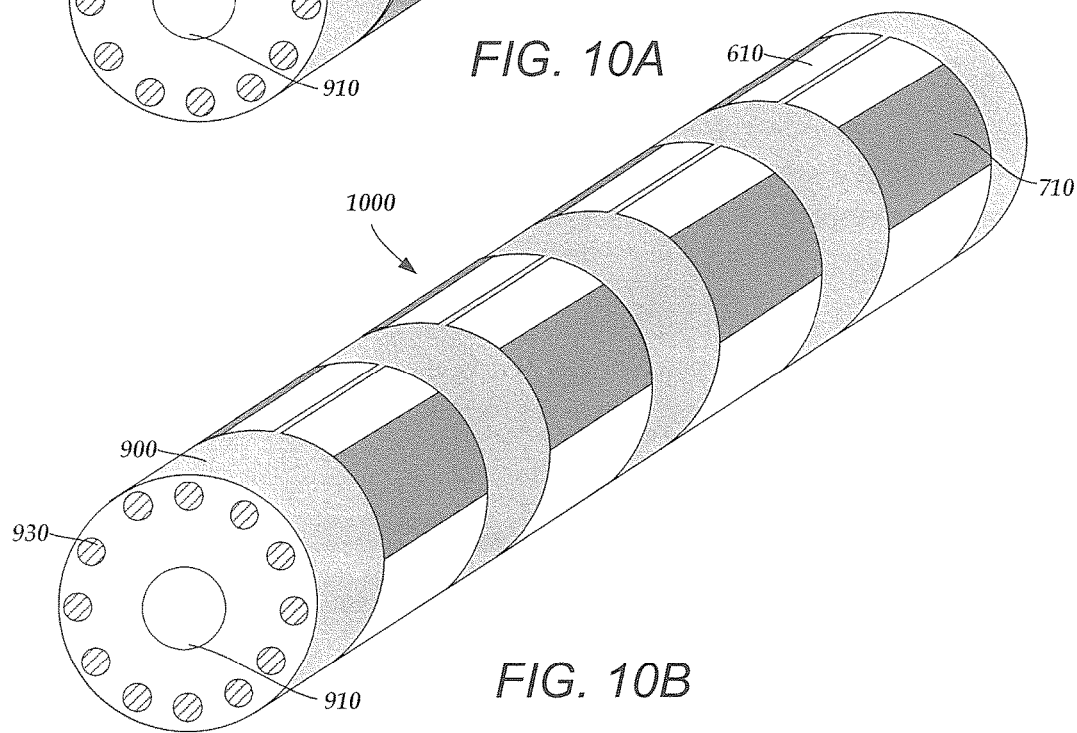
FIG. 10B is a schematic perspective view of the lead of FIG. 10A after removing portions of the electrode frame, according to the invention.

As seen in FIG. 10B, portions of the outer surface of the electrode frame 610 may also be removed (e.g., by ablation, grinding, and the like) to expose the segmented electrode 710. The outer surfaces of the electrode frames 610 may be removed in any pattern as desired. For example, in some embodiments, the outer surface of the electrode frame 610 is removed at one or more positions corresponding to each of the segmented electrodes 710 that are housed within. In at least some embodiments, an isodiametric lead is formed by grinding the outer surface of the electrode frame 610 and the lead body to the same diameter. When the outer surface of the electrode frame 610 is removed, the outer portion of the electrode chamber 620 is removed to form an electrode cavity and the electrodes 710 are exposed at the surface of the lead. In at least some embodiments, each segmented electrode 710 is electrically coupled to an independent conductor (not shown) disposed within one of the lumens 930 so that each segmented electrode 710 may be independently activated.

Figure 11A:
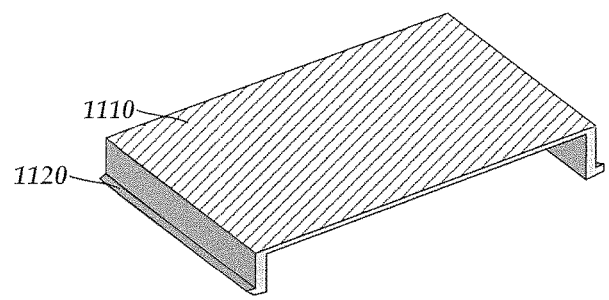
FIG. 11A is a schematic perspective view of one embodiment of an electrode having flanges, according to the invention.

Liquid injected molding may also be used to create a lead array. FIG. 11A is a schematic perspective view of one embodiment of a segmented electrode 1110. The segmented electrode 1110 may be similar to those described in other embodiments. In some embodiments, the segmented electrode 1110 is a rectangular portion having legs and includes flanges 1120. In some embodiments, each segmented electrode 1110 includes one flange 1120 on each side, though it will be understood that the segmented electrode 1110 may include any number of flanges 1120.

Figure 11B:
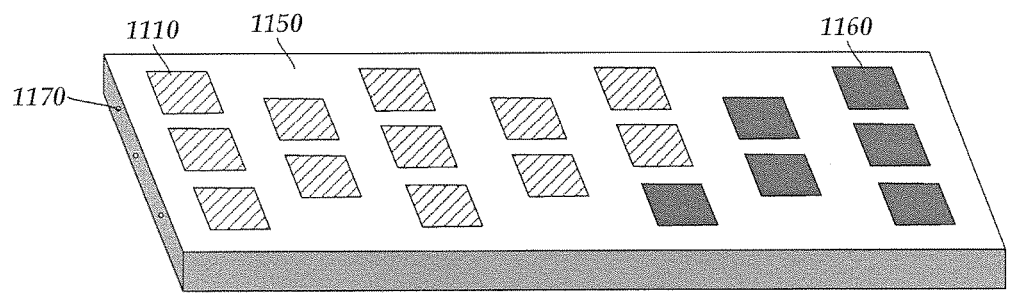
FIG. 11B is a schematic perspective view of one embodiment of the electrodes of FIG. 11A disposed in a carrier, according to the invention.

FIG. 11B is a schematic perspective view of one embodiment of the segmented electrode 1110 of FIG. 11A disposed in a carrier 1150. The carrier 1150 may be a tray-like member formed of any suitable insulative material capable of housing the segmented electrodes 1110. Suitable materials for the carrier 1150 include, but are not limited to polymers (including plastics), composite materials, and the like. In some embodiments, the carrier 1150 is formed of silicone. The carrier 1150 includes apertures 1160 for receiving the segmented electrodes 1110. In some embodiments, the apertures 1160 are formed of the same or different shapes and sizes. In some embodiments, the apertures 1160 correspond to the size and shape of the segmented electrodes 1110. Furthermore, the apertures 1160 may be formed in any pattern along the surface of the carrier 1150.

The carrier 1150 may also include side holes 1170 to allow for the passage of conductors (not shown) to the segmented electrodes 1110. In some embodiments, each aperture 1160 corresponds to one or more side holes 1170. The side holes 1170 may be formed in any edge or face of the carrier 1150. In some embodiments, as seen in FIG. 11B, the side holes 1170 are aligned along one edge of the carrier 1150. It will be understood that any number of side holes 1170 may be formed in the carrier 1150 in any pattern or alignment, such as in multiple rows.

Figure 11C:
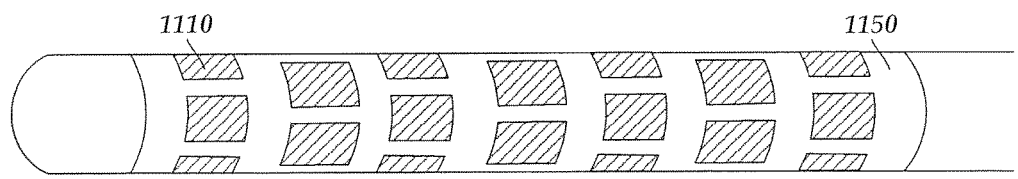
FIG. 11C is a schematic side view of one embodiment of the carrier of FIG. 11B after being wrapped to form a lead, according to the invention.

As seen in FIG. 11B, the segmented electrodes 1110 may be press fit into the apertures 1160 of the carrier 1150. In some embodiments, the segmented electrodes 1110 are locked in place by the flanges 1120 on the sides. The flanges 1120 may be configured to mate with a side of the apertures 1160. With the segmented electrodes 1110 locked in place, the carrier 1150 may be wrapped around a mandrel and reflowed to form a lead as seen in FIG. 11C.

In another embodiment, a tubing 1200 similar to that of the multi-lumen tubing 900 is provided. The tubing 1200 may be provided with a plurality of conductor lumens 1220. The tubing 1200 may also include a central passage 1210 configured for receiving an insertion instrument such as a stylet. Pre-welded electrode tubes 1250 may be disposed within the conductor lumens 1220.

Figure 12A:
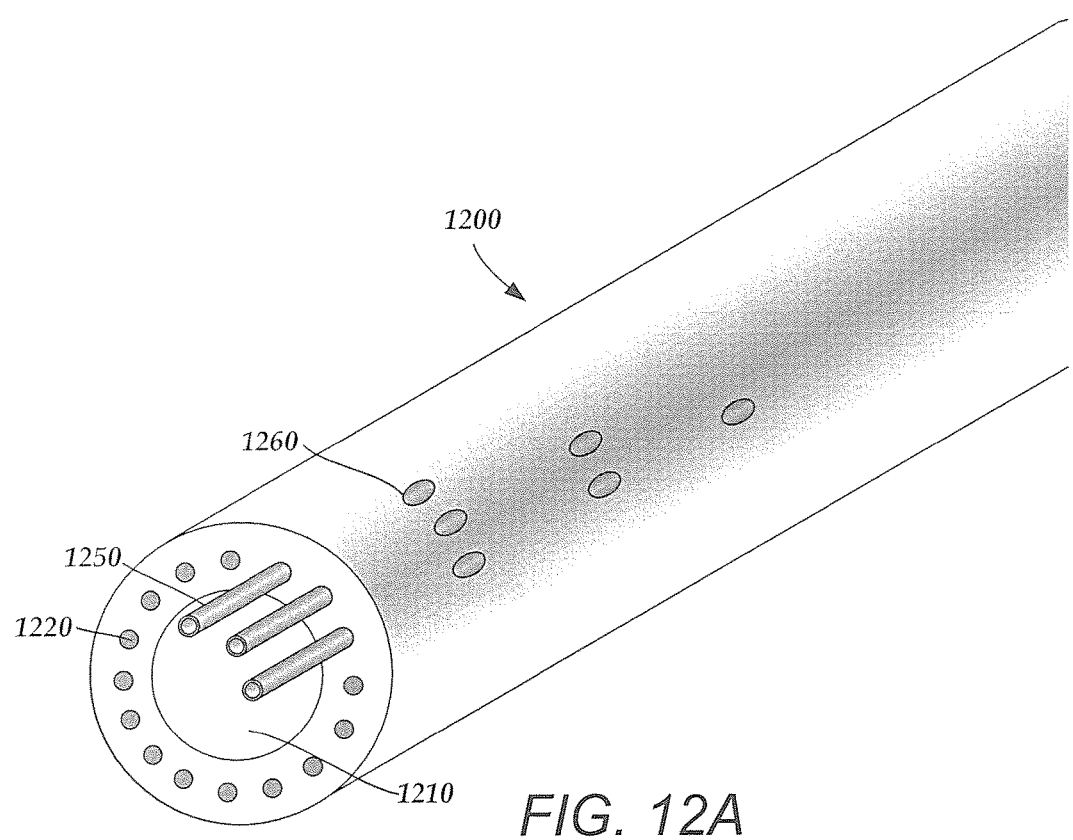
FIG. 12A is a schematic perspective view of one embodiment of a lead body having electrode tubes, according to the invention.

FIG. 12A is a schematic perspective view of one embodiment of a tubing 1200 having electrode tubes 1250. The electrode tubes 1250 may be short in length and inserted only in conductor lumens on sides of the multi-lumen tubing 1200 where stimulation is desired. In some embodiments, electrodes tubes 1250 are inserted only at the extremities of the multi-lumen tubing 1200. The electrode tubes 1250 may be press fit within the multi-lumen tubing 1200 to avoid slippage during manufacture and usage. In some embodiments, additional methods may be used to enhance coupling between the electrodes tubes 1250 and the multi-lumen tubing 1200, such as, for example, the use of epoxy within the conductor lumens 1220.

Figure 12B:
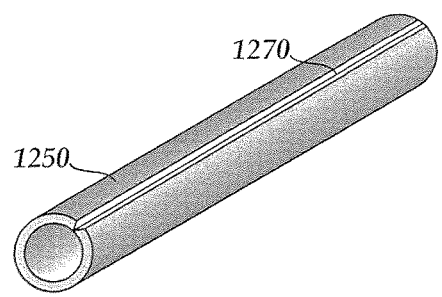
FIG. 12B is a schematic perspective view of one embodiment of an electrode tube having a groove, according to the invention.

In some embodiment, the electrode tubes 1250 have a groove 1270 that may be useful in coupling the electrode tube 1250 to the tubing 1200. As seen in FIG. 12B, the groove 1270 may be longitudinally positioned along the electrode tube 1250. Moreover, the conductor lumen 1220 may be defined to have a cross-sectional shape that will aid in fastening the electrode tube 1250 to the tubing 1200. It will be understood that any number of grooves 1270 may be positioned on the electrode tube 1250.

With the electrode tubes 1250 disposed within the multi-lumen tubing 1200, techniques such as grinding or ablation may be used to expose portions of the electrode tubes 1250 by removing portions of the outer surface of the tubing 1200. As seen in FIG. 12A, the locations of ablation 1260 may be chosen in any pattern as desired.

Modifications of these methods are possible. For example, one or more combinations of the above methods may be used to form a lead as desired. In some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of manufacturing a device for brain stimulation, the method comprising:
    forming a lead body having a distal end section;
    coupling at least one pre-electrode to the distal end section of the lead body, the pre-electrode defining a divider with a plurality of partitioning arms and having a plurality of fixing lumens;
    removing portions of the pre-electrode aligned with the partitioning arms to divide the pre-electrode into a plurality of segmented electrodes, each of the plurality of segmented electrodes defining at least one of the plurality of fixing lumens at least partially disposed through the segmented electrode; and
    introducing a material through the plurality of fixing lumens to couple the plurality of segmented electrodes to the lead body.

2. The method of claim 1, wherein each of the plurality of fixing lumens is a through hole.

3. The method of claim 1, wherein each of the plurality of segmented electrodes further defines at least one conductor lumen.

4. The method of claim 3, further comprising disposing at least one conductor within each of the at least one conductor lumen.

5. The method of claim 1, wherein introducing a material comprises reflowing a portion of the lead body through the plurality of fixing lumens.

6. The method of claim 1, wherein the divider has exactly three partitioning arms.

7. The method of claim 1, wherein the divider further defines a central lumen.

8. The method of claim 1, wherein removing the portions of the pre-electrode comprises grinding the pre-electrode to remove the portions of the pre-electrode and divide the pre-electrode into the plurality of segmented electrodes.

9. The method of claim 8, wherein grinding the pre-electrode comprises grinding the pre-electrode so that the plurality of segmented electrodes and lead body are isodiametric.

10. The method of claim 1, wherein removing the portions of the pre-electrode occurs after introducing the material through the plurality of fixing lumens.

11. The method of claim 1, wherein the plurality of fixing lumens extend only partially through the pre-electrode.

12. The method of claim 1, wherein the at least one fixing lumen is a plurality of fixing lumens with at least one of the fixing lumens defined within each of the segmented electrodes.

13. The method of claim 1, further comprising coupling at least one conductor to each of the plurality of segmented electrodes.

* * * * *